(12) United States Patent
Chi et al.

(10) Patent No.: US 9,040,702 B1
(45) Date of Patent: May 26, 2015

(54) LUMINESCENT PLATINUM(II) COMPLEXES WITH BIAZOLATE CHELATES

(71) Applicant: NATIONAL TSING HUA UNIVERSITY, Hsinchu (TW)

(72) Inventors: Yun Chi, Hsinchu (TW); Hsiu-Hsuan Yeh, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/277,117

(22) Filed: May 14, 2014

(30) Foreign Application Priority Data

Jan. 7, 2014 (TW) .............................. 103100509 A

(51) Int. Cl.
*C07F 15/00* (2006.01)
*H01L 51/00* (2006.01)
*H01L 51/50* (2006.01)

(52) U.S. Cl.
CPC ......... *H01L 51/0087* (2013.01); *H01L 51/5016* (2013.01); *H01L 51/5004* (2013.01)

(58) Field of Classification Search
USPC ...................................... 546/2; 548/101, 108
See application file for complete search history.

(56) References Cited

U.S. PATENT DOCUMENTS 8,889,872 B2 * 11/2014 Chi et al. ................... 546/268.1

* cited by examiner

*Primary Examiner* — Charanjit Aulakh
(74) *Attorney, Agent, or Firm* — Birch, Stewart, Kolasch & Birch, LLP

(57) ABSTRACT

A platinum complex of a formula (I):

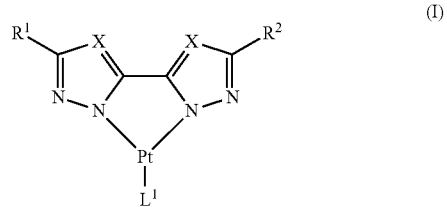

where
$R^1$ and $R^2$ are each fluoroalkyl,
X is C—H or nitrogen, and
$L^1$ is a bidentate, nitrogen-containing heteroaromatic ligand.

8 Claims, No Drawings

LUMINESCENT PLATINUM(II) COMPLEXES WITH BIAZOLATE CHELATES

CROSS-REFERENCE TO RELATED APPLICATION

This application claims priority of Taiwanese application no. 103100509, filed on Jan. 7, 2014.

BACKGROUND OF THE INVENTION

1. Field of the Invention

This invention relates to a platinum complex for an organic light-emitting diode, more particularly to a phosphorescent platinum complex having a dianionic bidentate ligand and a bidentate, nitrogen-containing heteroaromatic ligand.

2. Description of the Related Art

An organic electroluminescence device normally includes an organic light-emitting diode (OLED) and a driving element. An OLED includes an anode, a cathode, and an organic layer (i.e., light-emitting layer) disposed therebetween for emitting light when a voltage is applied between the anode and the cathode. Generally, the organic layer is made from a phosphorescent material, since phosphorescent material is able to emit light as a consequence of decaying of excitons from triplet state to ground state. As such, it is desirable to improve the phosphorescent organic layer so as to enhance the light-emitting efficiency of OLEDs. The inventor of the present invention previously disclosed in U.S. Pat. No. 7,002,013 a phosphorescent platinum complex with the following general formula (A):

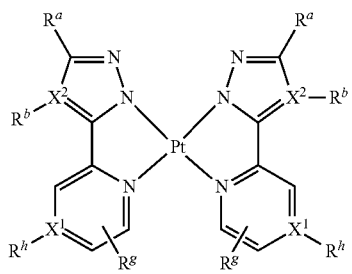

where $X^1$ and $X^2$ are each independently C or N, $X^1$ can also be located at another position of the hexagonal ring, when $X^1$ is N, $R^a$ is H, C1-C8 alkyl, or C1-C4 perfluoroalkyl, $R^b$ is H, $R^a$ and $R^b$ together are C4-C8 alkylene, or $R^a$ and $R^b$ together are bridged carbocyclic C4-C12 alkylene, when $X^2$ is C, $R^a$ is H, C1-C8 alkyl, or C1-C4 perfluoroalkyl, and $R^b$ is omitted, when $X^2$ is N, $R^g$ is H or methyl, and $R^h$ is omitted, when $X^1$ is N, and $R^g$ is H or methyl, and $R^h$ is H or methyl, or $R^g$ and $R^h$ together are

when $X^1$ is C.

The platinum complex is electroneutral, and the two ligands thereof are the same. Thus, it is difficult to fine-tune an energy gap between the highest occupied molecular orbital (HOMO) and the lowest unoccupied molecular orbital (LUMO) for tuning an emission wavelength.

SUMMARY OF THE INVENTION

An object of the present invention is to provide a novel phosphorescent platinum complex in which a suitable energy gap can be formed between the highest occupied molecular orbital (HOMO) and the lowest unoccupied molecular orbital (LUMO) of different bidentate ligands.

Accordingly, a platinum complex of this invention has the following formula (I):

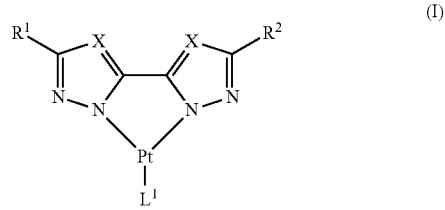

where $R^1$ and $R^2$ are each fluoroalkyl, X is C—H or nitrogen, and $L^1$ is a bidentate, nitrogen-containing heteroaromatic ligand.

DETAILED DESCRIPTION OF THE PREFERRED EMBODIMENTS

A phosphorescent platinum complex of the preferred embodiment of this invention has a formula (I):

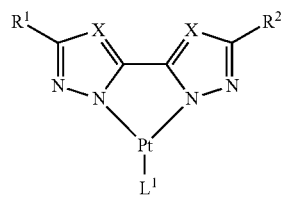

where $R^1$ and $R^2$ are each fluoroalkyl, X is C—H or nitrogen, and $L^1$ is a bidentate, nitrogen-containing heteroaromatic ligand.

The phosphorescent platinum complex is electroneutral, and has a dianionic bidentate ligand with a formula of

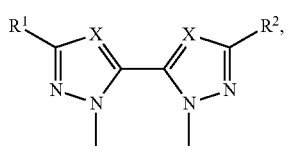

in which $R^1$ and $R^2$ are each fluoroalkyl which is a strong electron withdrawing group. Due to the presence of the strong electron withdrawing groups in the dianionic bidentate ligand, energy level of the highest occupied molecular orbital (HOMO) of the complex can be increased for the dianionic bidentate ligand, thereby increasing the energy gap between the HOMO contributed by the dianionic bidentate ligand and the lowest unoccupied molecular orbital (LUMO) contributed by $L^1$ to the extent that, as a result of relaxation, the wavelength of emission can fall within the visible range. When a specific dianionic bidentate ligand is selected, the emission color of the phosphorescent platinum complex can be desirably tuned by selecting substituents attached to carbon atoms of the bidentate, nitrogen-containing heteroaromatic ligand (L$^1$). Thus, in this invention, it is possible to fine-tune the energy gap between the HOMO and the LUMO of the phosphorescent platinum complex for the sake of tuning emission wavelength. Moreover, when the platinum complex serves as an emitting material of organic light-emitting diode (OLED), the OLED is anticipated to have good light-emitting efficiency.

Preferably, L$^1$ is

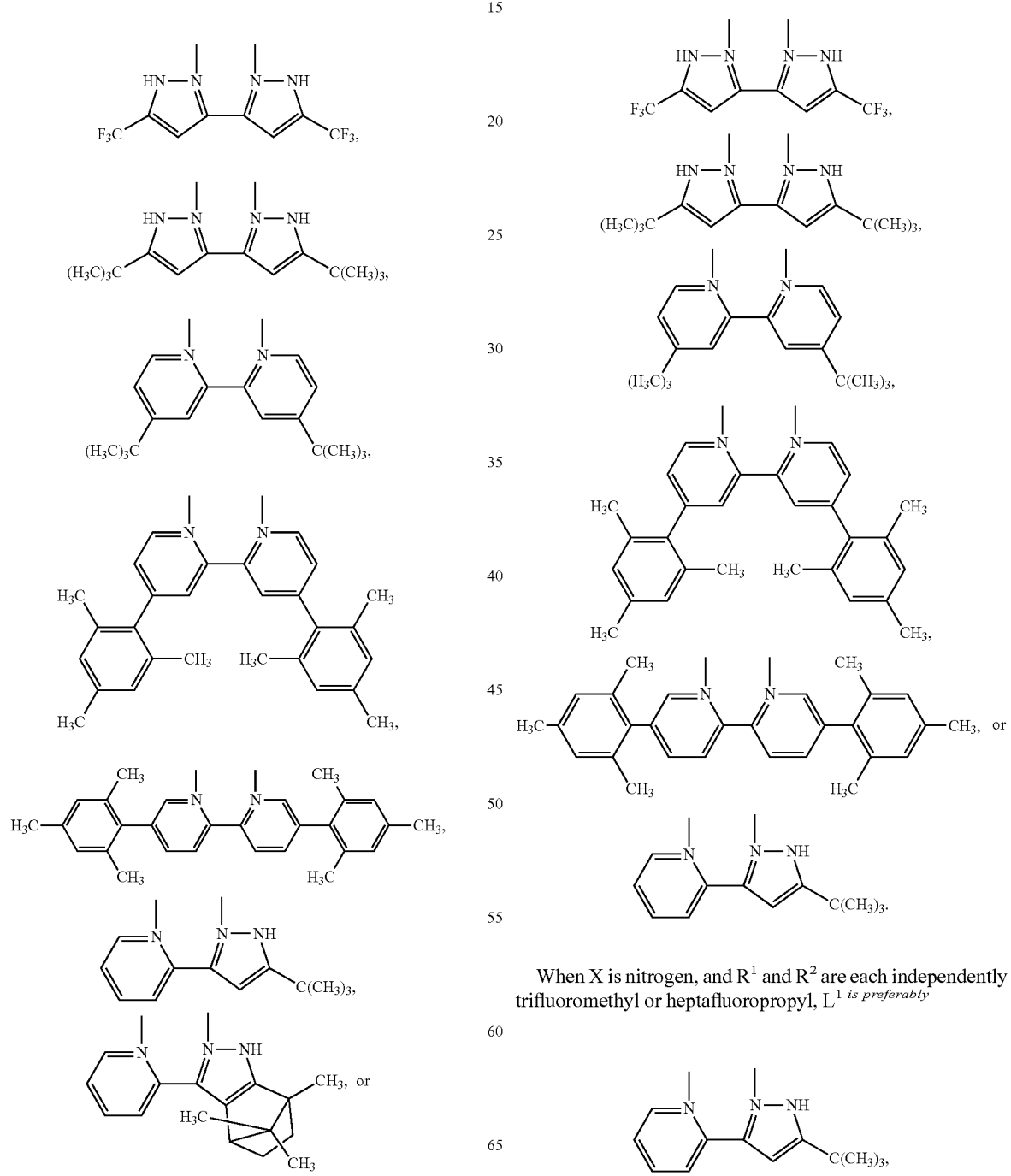

When X is C—H, and R$^1$ and R$^2$ are each independently trifluoromethyl or heptafluoropropyl, L$^1$ is preferably When X is nitrogen, and R$^1$ and R$^2$ are each independently trifluoromethyl or heptafluoropropyl, L$^1$ is preferably

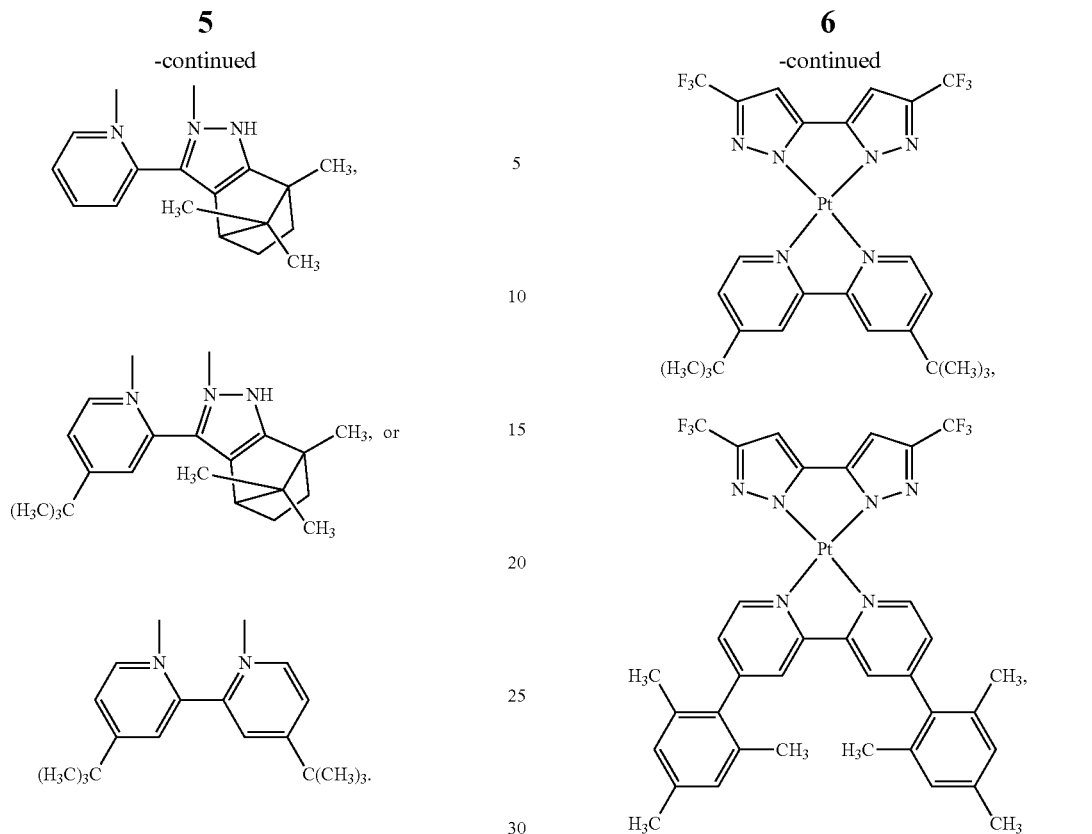
In this preferred embodiment, examples of the platinum complex include
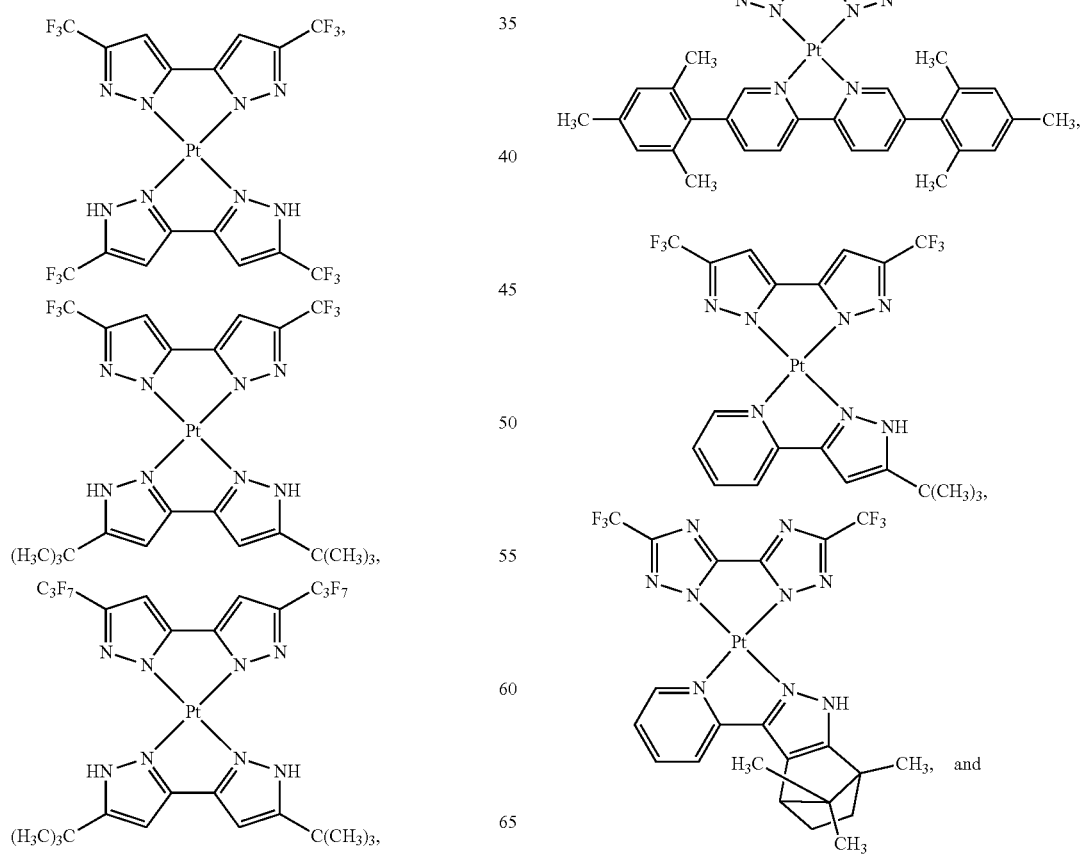

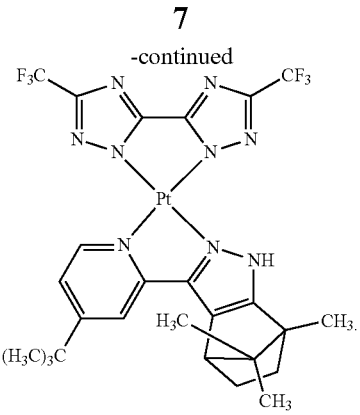

The platinum complex can be synthesized using adequate reactants and under adequate conditions so as to permit the platinum complex to have the desired properties. In this embodiment, the platinum complex is made by heating a mixture of a platinum source material and a biazole-based compound. The biazole-based compound has been disclosed in the applicant's co-pending application (US 2013/0296567 A1), which is incorporated herein by reference for all purposes. The biazole-based compound has the following formula (II):

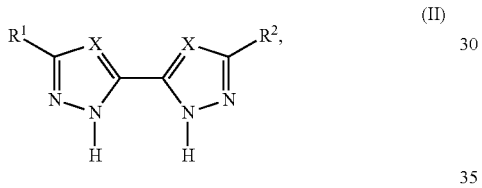

(II)

where $R^1$, $R^2$ and X are the same as those defined above.

The platinum source material is $Pt(DMSO)_2Cl_2$ (DMSO=dimethyl sulfoxide), potassium tetrachloroplatinate (II) ($K_2PtCl_4$), or

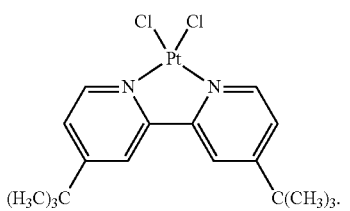

In one preferred embodiment, the platinum complex is made by the steps of: (1) heating a mixture of platinum source material and a nitrogen-containing heterocyclic compound to obtain an intermediate product, and (2) heating a mixture of the intermediate product and a biazole-based compound in the presence of a base promoter. The nitrogen-containing heterocyclic compound is

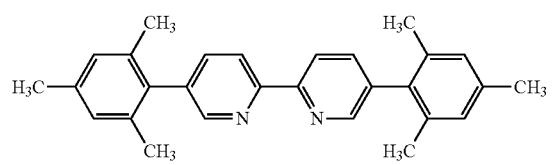

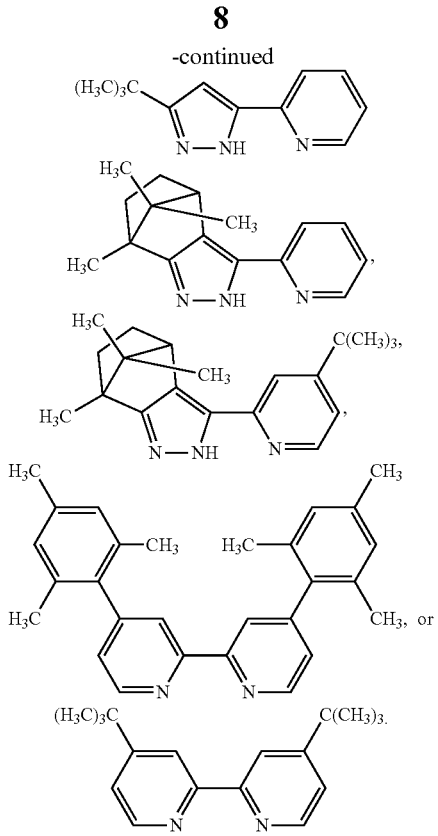

The platinum source material is $Pt(DMSO)_2Cl_2$ (DMSO=dimethyl sulfoxide), potassium tetrachloroplatinate (II) ($K_2PtCl_4$), or

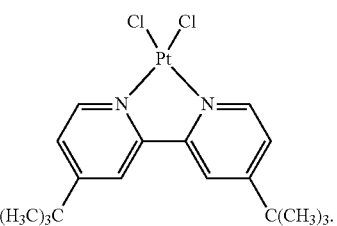

The biazole-based compound has the following formula (II):

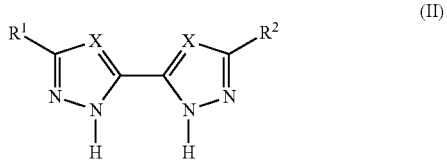

(II)

where $R^1$, $R^2$ and X are the same as those defined above.

The solvent can be any solvents that can dissolve the intermediate and the biazole-based compound, or any solvents that permit the reaction between the intermediate and the biazole-based compound to be carried out in a homogeneous phase. Non-limiting examples of the solvent include 2-methoxyethanol, dimethoxyethane, etc. The base promoter is used for promoting the reaction between the intermediate and the biazole-based compound. Non-limiting examples of the base promoter include sodium carbonate, sodium acetate, etc.

The present invention will now be explained in more detail below by way of the following examples.

Preparation of Phosphorescent Platinum Complex

Example 1 (EX 1)

$Pt(DMSO)_2Cl_2$ (100 mg, 0.24 mmol),

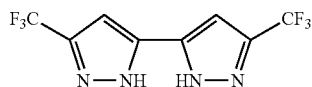

(127 mg, 0.48 mmol), and sodium carbonate (251 mg, 2.37 mmol) were dissolved in 50 ml acetone to obtain a mixture. The mixture was heated to reflux for 8 hours to obtain a crude solid product. This crude solid was then dissolved in ethyl acetate and washed with 50 ml deionized water for three times, followed by recrystallization from a mixture of dichloromethane and methanol to obtain a colorless solid (119 mg, 0.17 mmol, 73% yield) (hereinafter referred to as complex A).

The spectrum analysis for the complex A is: MS (FAB.$^{195}$Pt) m/z (real value): 732(733) [M–1]$^+$; $^1$H-NMR (400 MHz, acetone-$d_6$, 294 K), δ(ppm): 6.69 (s, 4H); $^{19}$F-NMR (470 MHz, CDCl$_3$, 294 K), δ(ppm): −60.87 (s, CF$_3$).

The chemical structure of the complex A was confirmed to be

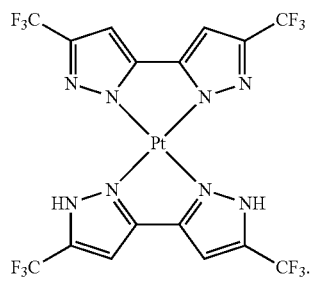

Example 2 (EX 2)

$K_2PtCl_4$ (1.802 g 4.34 mmol) and

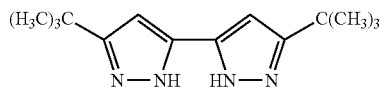

(1.070 g, 4.34 mmol) were disposed in a 150 ml reaction flask. 50 ml acetone and 50 ml hydrogen chloride solution (0.2N) were added thereto to obtain a first mixture. The first mixture was heated to reflux and under nitrogen atmosphere for a reaction period of 2 hours. After the reaction was complete and the temperature was cooled to room temperature, the yellow precipitate was collected and washed with deionized water, followed by drying under vacuum.

Next, the yellow precipitate (700 mg, 1.37 mmol) was disposed in a 50 ml reaction flask, and

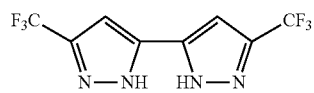

(369 mg, 1.37 mmol), Ag$_2$O (473 mg, 2.05 mmol), and 100 ml toluene were added thereto to obtain a second mixture. The second mixture was heated to reflux for a reaction period of 1 day. After the reaction was complete, the second mixture was filtered using a pad of celite, and the filtrate was evaporated to dryness. The obtained residue was next purified by column chromatography, using a mixture of ethyl acetate and hexane (ethyl acetate:hexane=1:1) as an eluent, to obtain a colorless solid (397 mg, 0.56 mmol, 41% yield) (hereinafter referred to as complex B).

The spectrum analysis for the complex B is: MS (FAB. $^{195}$Pt) m/z (real value): 709(710) [M–1]$^+$; $^1$H-NMR (400 MHz, acetone-$d_6$, 294 K), δ(Ppm): 6.89 (s, 2H), 6.76 (s, 2H), 1.49 (s, 9H); $^{19}$F-NMR (470 MHz, CDCl$_3$, 294 K), δ(ppm): −60.92 (s, CF$_3$); $C_{22}H_{24}F_6N_8Pt \cdot H_2O$ (analysis value): C, 36.32; N, 15.4; H, 3.6; (experimental value): C, 36.35; N, 15.03; H, 3.86.

The chemical structure of the complex B was confirmed to be

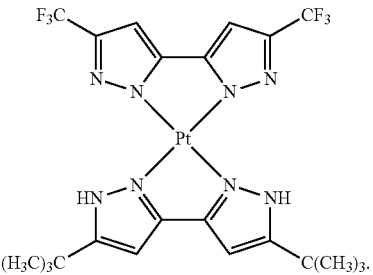

Example 3 (EX 3)

$K_2PtCl_4$ (1.802 g, 4.34 mmol) and

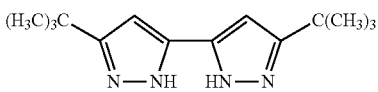 [SMILES: CC(C)(C)c1cc(-c2cc(C(C)(C)C)n[nH]2)[nH]n1]

(1.070 g, 4.34 mmol) were disposed in a 150 ml reaction flask. 50 ml acetone and 50 ml hydrogen chloride solution (0.2 N) were added thereto to obtain a mixture. This first mixture was heated to reflux and under nitrogen atmosphere for a period of 2 hours. After the reaction was completed and the temperature was cooled to room temperature, the yellow precipitate was filtered and then washed with deionized water 3 times.

Next, the yellow precipitate (500 mg, 0.98 mmol) was disposed in a 50 ml reaction flask, and

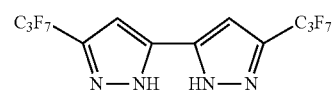

(459 mg, 0.98 mmol), Ag$_2$O (338 mg, 1.46 mmol), and 100 ml toluene were added thereto to obtain a second mixture. The second mixture was heated to reflux for a period of 1 day. After the reaction was completed, the solution was filtered using a pad of celite and the collected filtrate was evaporated to dryness. The obtained residue was purified by column chromatography, using a mixture of ethyl acetate and hexane (ethyl acetate:hexane=1:1) as an eluent, to obtain a colorless solid (382 mg, 0.420 mmol, 43% yield) (hereinafter referred to as complex C).

The spectrum analysis for the complex C is: MS (FAB. $^{195}$Pt) m/z (real value): 909(910) [M−1]$^+$; $^1$H-NMR (400 MHz, CD$_2$Cl$_2$, 294 K), δ(Ppm): 6.90 (s, 2H), 6.83 (s, 2H), 1.48 (s, 9H); $^{19}$F-NMR (470 MHz, CDCl$_3$, 294 K), δ(ppm): −82.72 (t, $^3J_{HH}$=11.8 Hz, CF$_3$), −111.95 (m, CF$_2$), −129.49 (s, CF$_2$); C$_{26}$H$_{24}$F$_{14}$N$_8$Pt.H$_2$O (analysis value): C, 33.67; N, 12.08; H, 2.83; (experimental value): C, 33.55; N, 11.65; H, 3.09.

The chemical structure of the complex C was confirmed to be

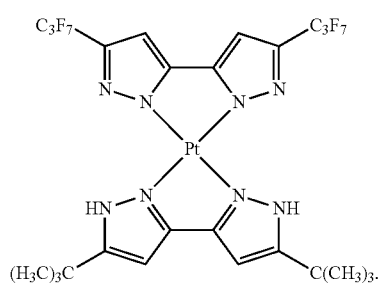

Example 4 (EX 4)

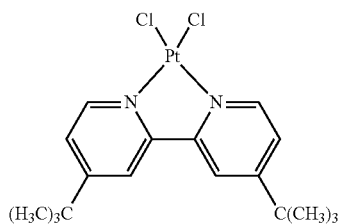

(300 mg, 0.56 mmol),

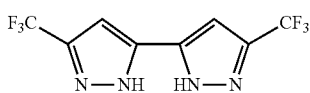 [SMILES: FC(F)(F)c1cc(-c2cc(C(F)(F)F)n[nH]2)[nH]n1]

(167 mg, 0.62 mmol), and sodium acetate (459 mg, 5.60 mmol) were dissolved in 50 ml 2-methoxyethanol to obtain a mixture. The mixture was heated to reflux for a period of 8 hours. After the reaction was completed and the temperature was cooled to room temperature, 50 ml deionized water was added to the solution to induce a precipitation. The collected precipitate was then recrystallized from a mixture of dichloromethane and acetone to obtain an orange solid (255 mg, 0.35 mmol, 62% yield) (hereinafter referred to as complex D).

The spectrum analysis for the complex D is: MS (FAB. $^{195}$Pt) m/z (real value): 732 (731) [M+1]$^+$; $^1$H-NMR (400 MHz, CDCl$_3$, 294 K), δ (ppm): 10.49 (d, $^3J_{HH}$=6 Hz, 2H), 8.65 (s, 2H), 7.98 (d, $^3J_{HH}$=6 Hz, 2H), 6.72 (s, 2H), 1.46 (s, 18H); $^{19}$F-NMR (470 MHz, CDCl$_3$, 294 K), δ(ppm): −60.58 (s, CF$_3$)

The chemical structure of the complex D was confirmed to be

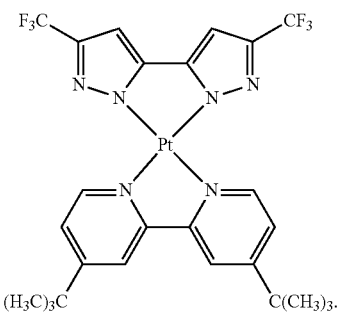

Example 5 (EX5)

Pt(DMSO)$_2$Cl$_2$ (500 mg, 1.19 mmol) and

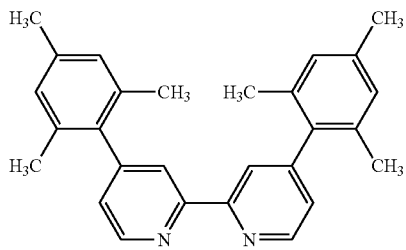 [SMILES: Cc1cc(C)c(-c2ccnc(-c3cc(-c4c(C)cc(C)cc4C)ccn3)c2)c(C)c1]

(464 mg, 1.19 mmol) were dissolved in 100 ml 2-methoxyethanol to obtain a mixture. The mixture was heated to reflux for a period of 2 hours. After the reaction was completed and the temperature was cooled to room temperature,

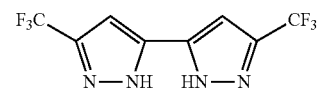 [SMILES: FC(F)(F)c1cc(-c2cc(C(F)(F)F)n[nH]2)[nH]n1]

(317 mg, 1.19 mmol) and sodium acetate (972 mg, 11.85 mmol) were added to the solution, followed by heating under reflux for 8 hours to obtain a crude solid. This crude product was washed with deionized water and purified by column chromatography, in which a mixture of dichloromethane and hexane (dichloromethane: hexane=1:1) was used as an eluent, to obtain a yellow green solid (734 mg, 0.86 mmol, 73% yield) (hereinafter referred to as complex E).

The spectrum analysis for the complex E is: MS (FAB. $^{195}$Pt) m/z (real value): 856 (855) [M+1]$^+$; $^1$H-NMR (400 MHz, CDCl$_3$, 294 K), δ(ppm): 11.13 (d, $^3J_{HH}$=6 Hz, 2H), 7.77 (s, 2H), 7.59 (d, $^3J_{HH}$=6 Hz, 2H), 6.98 (s, 4H), 6.59 (s, 2H), 2.33 (s, 6H), 2.06 (s, 12H); $^{19}$F-NMR (470 MHz, CDCl$_3$, 294 K), δ(ppm): −60.7 (s, CF$_3$); C$_{36}$H$_{30}$F$_6$N$_6$Pt (analysis value): C, 50.53; N, 9.82; H, 3.53; (experimental value): C, 50.19; N, 9.73; H, 3.77.

The chemical structure of the complex E was confirmed to be

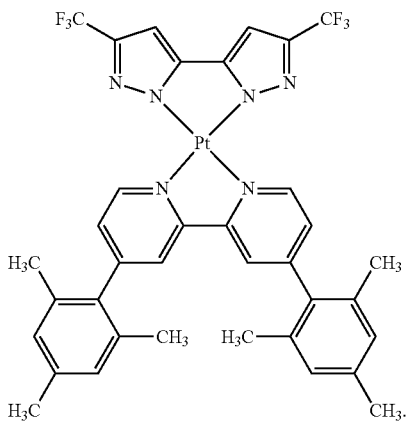

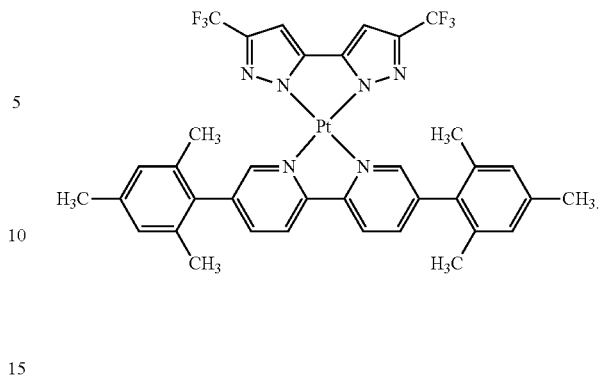

Example 7 (EX 7)

K$_2$PtCl$_4$ (489 mg, 1.17 mmol) and

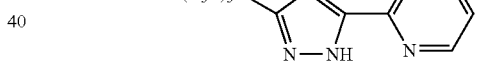

Example 6 (EX 6)

Pt(DMSO)$_2$Cl$_2$ (50 mg, 0.12 mmol) and

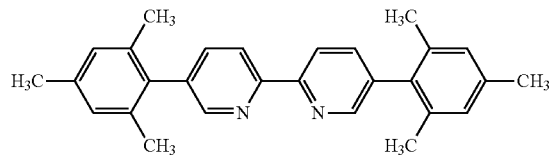

(47 mg, 0.12 mmol) were dissolved in 50 ml 2-methoxyethanol to obtain a reaction mixture. The mixture was heated to reflux for a period of 8 hours. After the reaction was completed and the temperature was cooled to room temperature,

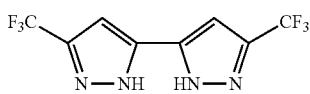 [SMILES: FC(F)(F)c1cc(-c2cc(C(F)(F)F)n[nH]2)[nH]n1]

(32 mg, 0.12 mmol) and sodium acetate (100.1 mg, 1.22 mmol) were added to the solution. It was then heated under reflux for 8 hours to obtain a crude solid product. The crude product was purified by column chromatography, using a mixture of dichloromethane and hexane (dichloromethane:hexane=1:1) as an eluent, to obtain a yellow green product (69 mg, 0.08 mmol, 68% yield) (hereinafter referred to as complex F).

The spectrum analysis for the complex F is: MS (FAB. $^{195}$Pt) m/z (real value): 856 (855) [M+1]$^+$; $^1$H-NMR (400 MHz, CDCl$_3$, 294 K), δ(ppm): 11.06 (s, 2H), 8.09 (d, $^3J_{HH}$=8 Hz, 2H), 8.05 (d, $^3J_{HH}$=8 Hz, 2H), 7.03 (s, 4H) 6.52 (s, 2H), 2.36 (s, 6H), 2.21 (s, 12H); $^{19}$F-NMR (470 MHz, CDCl$_3$, 294 K), δ(ppm): −61.02 (s, CF$_3$); C$_{36}$H$_{30}$F$_6$N$_6$Pt (analysis value): C, 50.53; N, 9.82; H, 3.53; (experimental value): C, 50.29; N, 9.82; H, 3.88.

The chemical structure of the complex F was confirmed to be (237 mg, 1.18 mmol) were dissolved in a solution including 20 ml hydrogen chloride solution (0.2 N) and 20 ml acetone to obtain a first mixture. The first mixture was heated and maintained at 80° C. for 2 hours, followed by collection of solid. The solid was washed with deionized water. Thereafter, the solid, (287 mg, 1.07 mmol), and Ag$_2$O (619 mg, 2.68 mmol) were dispersed in 100 ml toluene to obtain a second mixture. The second mixture was shaded by an aluminum foil and was heated to reflux for a period of 1 day. After the reaction was completed, the solution was filtered using a pad of celite and the collected filtrate was evaporated to dryness. The obtained residue was purified by column chromatography, eluting with pure dichloromethane, to obtain a yellow solid product (350 mg, 0.527 mmol, 49% yield) (hereinafter referred to as complex G).

The spectrum analysis for the complex G is: MS (FAB. $^{195}$Pt) m/z (real value): 665 (664) [M−1]$^+$; $^1$H-NMR (400 MHz, acetone-d$_6$, 294 K), δ(ppm): 9.98 (d, $^3J_{HH}$=5.6 Hz, 1H), 8.10 (dd, $^3J_{HH}$=8 Hz, $^3J_{HH}$=7.3 Hz, 1H), 7.75 (d, $^3J_{HH}$=8 Hz, 1H), 7.59 (dd, $^3J_{HH}$=7.2 Hz, $^3J_{HH}$=5.8 Hz, 1H), 6.62 (s, 1H), 6.56 (s, 1H), 6.52 (s, 1H), 1.48 (s, 9H); $^{19}$F-NMR (470 MHz, acetone-d$_6$, 294K), δ(ppm): −60.77 (s, CF$_3$), −61.53 (s, CF$_3$).

The chemical structure of the complex G was confirmed to be

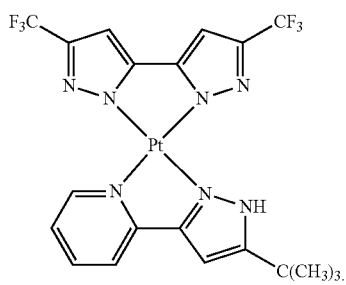
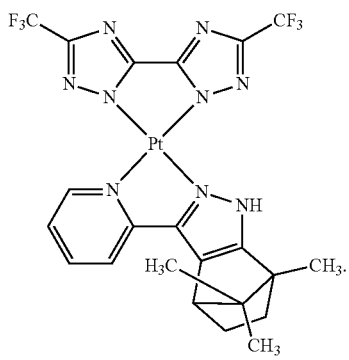

Example 8 (EX 8)

K$_2$PtCl$_4$ (168 mg, 0.41 mmol) and

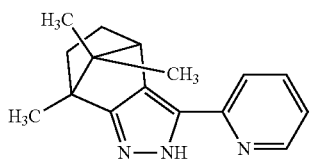 [SMILES: CC12CCC(c3c1n[nH]c3-c1ccccn1)C2(C)C]

(97 mg, 0.41 mmol) were dissolved in 20 ml hydrogen chloride solution (0.2 N) to obtain a first mixture. The first mixture was allowed to react at room temperature for 12 hours, followed by collection of precipitate. The precipitate was washed with deionized water. A solution including the precipitate,

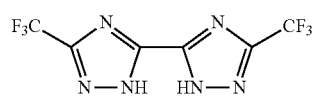

(110 mg, 0.41 mmol), sodium acetate (160 mg, 2.01 mmol), and 20 ml of 2-methoxyethanol was heated to reflux for 2 hours, followed by addition of 20 ml deionized water to induce precipitation. The collected precipitate was next purified by column chromatography and eluted with a mixture of dichloromethane and ethyl acetate (dichloromethane:ethyl acetate=6:1), to obtain a yellow solid (130 mg, 0.18 mmol, 46% yield) (hereinafter referred to as complex H).

The spectrum analysis for the complex H is: $^1$H-NMR (400 MHz, acetone-d$_6$, 294 K), δ(ppm): 11.05 (s, NH) 9.55 (d, $^3J_{HH}$=5.6 Hz, 1H), 8.32 (t, $^3J_{HH}$=7.6 Hz, 1H), 7.90 (d, $^3J_{HH}$=8 Hz, 1H), 7.69 (t, $^3J_{HH}$=6.0 Hz, 1H), 3.38 (d, $^3J_{HH}$=4.0 Hz, 1H), 2.26 (m, 1H), 2.02-1.99 (m, 2H) 1.57 (m, 1H), 1.43 (s, 3H), 1.09 (s, 3H), 0.73 (s, 3H); $^{19}$F-NMR (470 MHz, CD$_2$Cl$_2$, 294 K), δ(ppm): −64.14 (s, CF$_3$), −64.61 (s, CF$_3$).

The chemical structure of the complex H was confirmed to be

Example 9 (EX 9)

K$_2$PtCl$_4$ (194 mg, 0.47 mmol) and

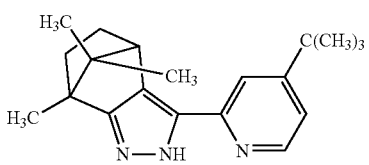

(145 mg, 0.47 mmol) were dissolved in 20 ml hydrogen chloride solution (0.2 N) to obtain a first mixture. The first mixture was allowed to react at room temperature for 12 hours to induce the formation of a precipitate, which was then washed with deionized water. This solid precipitate,

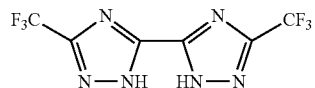

(127 mg, 0.47 mmol), and sodium acetate (160 mg, 2.01 mmol) were dispersed in 20 ml 2-methoxyethanol to obtain a second mixture. The second mixture was heated to reflux for 2 hours, followed by addition of 20 ml deionized water to induce precipitation. The collected precipitate was purified by column chromatography and eluted with a mixture of dichloromethane and ethyl acetate (dichloromethane:ethyl acetate=5:1), to obtain a yellow solid (152 mg, 0.20 mmol, 42% yield) (hereinafter referred to as complex I).

The spectrum analysis for the complex I is: $^1$H NMR (400 MHz, CD$_2$Cl$_2$, 294 K), δ(ppm): 11.05 (s, NH) 9.08 (d, $^3J_{HH}$=7.5 Hz, 1H), 7.39 (s, 1H), 7.34 (d, $^3J_{HH}$=7.5 Hz, 1H), 3.14 (d, $^3J_{HH}$=4.0 Hz, 1H), 2.26 (m, 1H), 2.02-1.99 (m, 2H), 1.44 (m, 9H), 1.43 (s, 3H), 1.09 (s, 3H), 0.73 (s, 3H); $^{19}$F-NMR (470 MHz, CD$_2$Cl$_2$, 294 K), δ(ppm): −65.25 (s, CF$_3$), −66.08 (s, CF$_3$).

The chemical structure of the complex I was confirmed to be

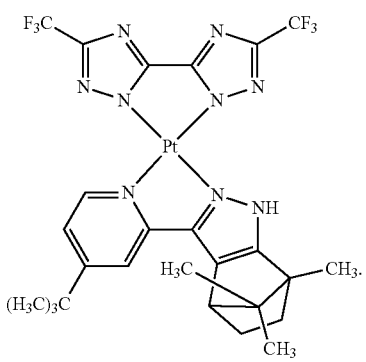

Preparation of Organic Light-Emitting Diode (OLED)

Example 10 (EX 10)

An anode substrate was prepared. The anode substrate included a glass substrate and an indium tin oxide (ITO) film that was formed on the glass substrate, that has a sheet resistance of 10 ohm/square, and that serves as an anode of an OLED. The anode substrate was cleaned by using an electronic grade cleaning agent such as deionized water, acetone, and methanol. The anode substrate was dried and cleaned by UV-ozone to enhance a work function of the ITO film and cleanness of the anode substrate.

Subsequently, a hole injection layer, a hole transport layer, an electron blocking layer, a light-emitting layer, and an electron transport layer were deposited on the anode substrate under a pressure of $2 \times 10^{-6}$ torr using a thermal evaporation device with multiple sources, to thereby obtain an organic light-emitting diode. The hole injection layer was made from poly(3,4-ethylene-dioxythiophene)-poly-(styrenesulfonate) (PEDOT:PSS) and had a thickness of 50 nm. The hole transport layer included a layer of N,N'-di(1-naphthyl)-N,N'-diphenyl-benzidine (NPB) (thickness: 20 nm) and a layer of 4,4',4"-tri(N-carbazolyl)triphenylamine (TCTA) (thickness: 5 nm) as both triplet exciton blocker and hole transporting material. The light-emitting layer included a host material [9-(3-iodobenzene)carbazole] doped with a guest material (the complex B made in Example 2) in a dopant concentration of 6%. The thickness of the light-emitting layer was 10 nm. The electron transport layer was made from diphenyl-bis[4-(pyridin-3-yl)phenyl]silane (DPPS), and had a thickness of 50 nm. LiF and Al served as the electron-injection layer and cathode, respectively.

Example 11 (EX 11)

An organic light-emitting diode was made according to the same procedures employed in Example 10, except that the guest material for the light-emitting layer was the complex C made in Example 3.

Example 12 (EX 12)

An organic light-emitting diode was made according to the same procedures employed in Example 10, except that the light-emitting layer included a host material (NPB) doped with a guest material (the complex D made in Example 4) in a dopant concentration of 60, and had a thickness of 10 nm, and that the electron transport layer was made from 4,7-diphenyl-1,10-phenanthroline (Bphen), and had a thickness of 50 nm.

Example 13 (EX 13)

An organic light-emitting diode was made according to the same procedures employed in Example 12, except that the host material was doped with a guest material (the complex D in Example 4) in a dopant concentration of 10%.

Example 14 (EX 14)

An organic light-emitting diode was made according to the same procedures employed in Example 13, except that the light-emitting layer had a thickness of 25 nm.

Test Items

<UV-Visible Spectrum>

A platinum complex was added to dichloromethane to prepare a test solution of a concentration of $10^{-5}$ M. Absorption spectrum of the test solution was measured using a UV-Visible Spectrophotometer (Hitachi Spectrophotometer; Model no.: U-3900). The spectra of the respective platinum complexes of Examples 1 to 8 are listed in the following Table 1.

<Fluorescence Spectrum>

A platinum complex was dissolved in 2-methyltetrahydrofuran at 77 K to prepare a test solution of $10^{-5}$ M. A fluorescence spectrum of the test solution at 77K was measured using a fluorescence spectrophotometer (Edinburgh Instruments FLS920). The emission wavelengths of Examples 1 to 8 are listed in Table 1.

A fluorescence spectrum of the powder (the platinum complex) at 25° C. was determined using a fluorescence spectrophotometer (Edinburgh Instruments FLS920). The emission wavelengths of the respective Examples 1 to 8 in the form of powder are listed in Table 1.

<Quantum Efficiency>

Quantum efficiency (i.e., quantum yield, Q.Y.) for the powder (the platinum complex) was measured at 25° C. using an integrating sphere (Edinburgh Instruments). The quantum efficiencies of the respective platinum complexes of Examples 1 to 8 are listed in Table 1.

<Testing for OLED>

An organic light-emitting diode (OLED) was tested in a glove box. Power was applied to the OLED, and a driving voltage ($V_{on}$) and a maximum current density ($I_{max}$) were recorded by virtue of a current-voltage meter. A luminous intensity of the OLED was measured using photodiodes (United Detector Technology (UDT), model: PIN-10DP), and a maximum brightness ($L_{max}$) of the OLED was calculated. Electroluminescence of the OLED was measured using a spectrometer (OTO Photonics Inc., model: SD1200). External quantum efficiency ($\eta_{ext}$) current efficiency ($\eta_c$) and power efficacy ($\eta_p$) of the OLED were calculated based on the above data. The CIE(x, y) coordinates of light emitted from the OLED were calculated from the spectral distribution of the light source and the CIE color-matching functions. The driving voltages ($V_{on}$), the maximum brightness ($L_{max}$), the maximum current densities ($I_{max}$), the external quantum efficiencies ($\eta_{ext}$) the current efficiencies ($\eta_c$) the power efficacies ($\eta_p$), and the x- and y-coordinate values of CIE(x, y) coordinates of the respective OLEDs of Examples 10 to 14 are listed in Table 2.

TABLE 1

| | UV/Vis spectrum $\lambda_{max}$ (nm) ϵ (ϵ × $10^{-3}$, M$^{-1}$ cm$^{-1}$) | Fluorescence spectrum $\lambda_{max}$ (nm) | Q.Y. (%) |
|---|---|---|---|
| EX 1 | 298 (15.1) 265 (9.9) | (407, 428, 460)$^a$ [394, 417, 441, 469]$^b$ | (10.3)$^a$ |
| EX 2 | 314 (8.5), 254 (10.8) | (450, 473, 514)$^a$ [416, 442, 471, 505]$^b$ | (4.3)$^a$ |
| EX 3 | 314 (9.0), 255 (10.9) | (431, 452, 477, 510)$^a$ [416, 442, 471, 505]$^b$ | (6.4)$^a$ |
| EX 4 | 377 (5.27), 265 (17.9) | (622)$^a$ [451, 483, 555]$^b$ | (75.6)$^a$ |
| EX 5 | 386 (8.0), 273 (25.2) | (547)$^a$ [475, 509, 546]$^b$ | (7.8)$^a$ |
| EX 6 | 356 (17.9), 267 (24.0) | (569)$^a$ [507, 547, 585]$^b$ | (7.2)$^a$ |
| EX 7 | 352 (7.4), 292 (8.9), 255 (15.0) | (502, 536)$^a$ [448, 477, 511]$^b$ | (29.8)$^a$ |
| EX 8 | 338 (9.3) 313 (15.4) | (526)$^a$ | (35.8)$^a$ |

$^a$Data for the powder samples (measured at 25° C.)
$^b$Data obtained in the frozen solution at 77 K.
Q.Y.: Quantum yield

TABLE 2

| | Light-emitting layer (nm) | Guest material | Dopant conc. | $V_{on}$ [V] | $L_{max}$ [cd/m$^2$] | $I_{max}$ [mA/cm$^2$] | $\eta$ext [%] | $\eta_c$ [cd/A] | $\eta_p$ [lm/W] | CIE [x, y] |
|---|---|---|---|---|---|---|---|---|---|---|
| EX 10 | 10 | Complex B (EX 2) | 6% | 4.5 | 800 (14.5 V) | 310 | 0.36 | 0.6 | 0.21 | 0.22, 0.26 |
| EX 11 | 10 | Complex C (EX 3) | 6% | 3.5 | 770 (14 V) | 305 | 0.63 | 1.0 | 0.64 | 0.19, 0.23 |
| EX 12 | 10 | Complex D (EX 4) | 6% | 3 | 14700 (12 V) | 730 | 12.2 | 20.1 | 18.1 | 0.57, 0.42 |
| EX 13 | 10 | | 10% | 3 | 14000 (12 V) | 620 | 12.8 | 17.8 | 14.0 | 0.59, 0.40 |
| EX 14 | 25 | | 10% | 3 | 16500 (17.5 V) | 550 | 13.7 | 21.1 | 16.6 | 0.58, 0.41 |

$V_{on}$: Driving voltage
$L_{max}$: Maximum brightness
$I_{max}$: Maximum current density
$\eta_{ext}$: External quantum efficiency
$\eta_c$: Current efficiency
$\eta_p$: Power efficacy From the results shown in Tables 1 and 2, it can be seen that the emission wavelength of the platinum complexes can be fine-tuned by different modifications of the dianionic ligands. All samples mentioned in this invention have good quantum efficiency (Q.Y.), and the OLEDs made from the platinum complexes of this invention can provide good performance in terms of maximum brightness, external quantum efficiency, current efficiency and power efficacy, and are comparable to conventional OLEDs (such as those disclosed in U.S. Pat. No. 7,002,013).

In sum, the platinum complex of this invention is electro-neutral, for which the associated HOMO and LUMO energy gap (i.e. emission peak wavelengths) can be fine-tuned by variation of the biazolate and neutral nitrogen-containing heteroaromatic ligands. Moreover, when the platinum complex serves as a material of a light-emitting layer of an organic light-emitting diode (OLED), the OLED is anticipated to have good light-emitting efficiency (i.e., good current efficiency and good power efficacy).

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

What is claimed is:

1. A platinum complex of a formula (I):

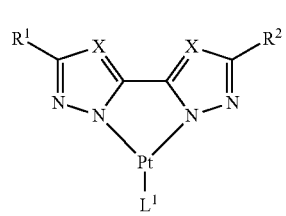

where $R^1$ and $R^2$ are each fluoroalkyl,

X is C—H or nitrogen, and $L^1$ is a bidentate, nitrogen-containing heteroaromatic ligand.

2. The platinum complex of claim 1, wherein $L^1$ is

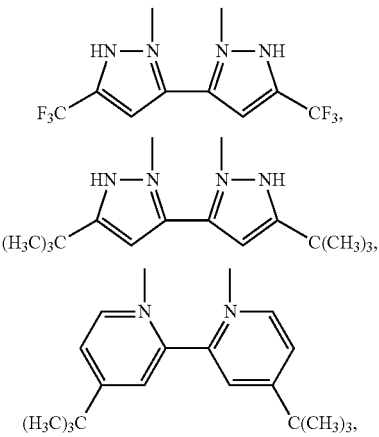

-continued

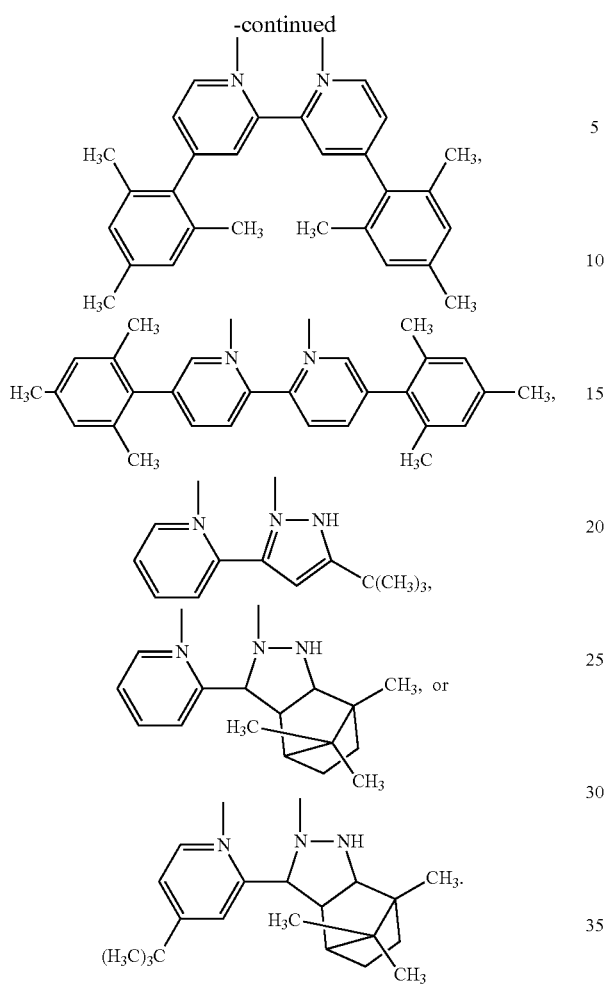

3. The platinum complex of claim 1, wherein X is C—H.
4. The platinum complex of claim 3, wherein $R^1$ and $R^2$ are each independently trifluoromethyl or heptafluoropropyl.
5. The platinum complex of claim 4, wherein $L^1$ is

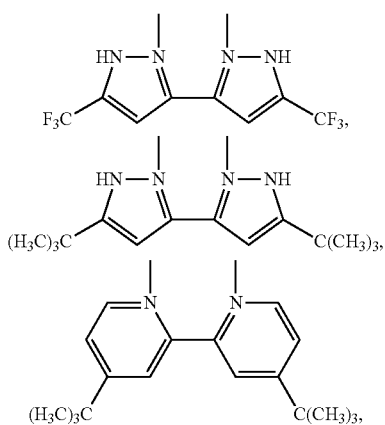

-continued

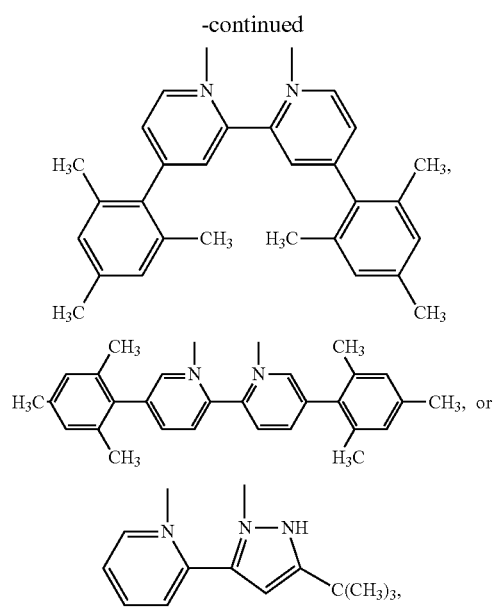

6. The platinum complex of claim 1, wherein X is nitrogen.
7. The platinum complex of claim 6, wherein $R^1$ and $R^2$ are each independently trifluoromethyl or heptafluoropropyl.
8. The platinum complex of claim 7, wherein $L^1$ is

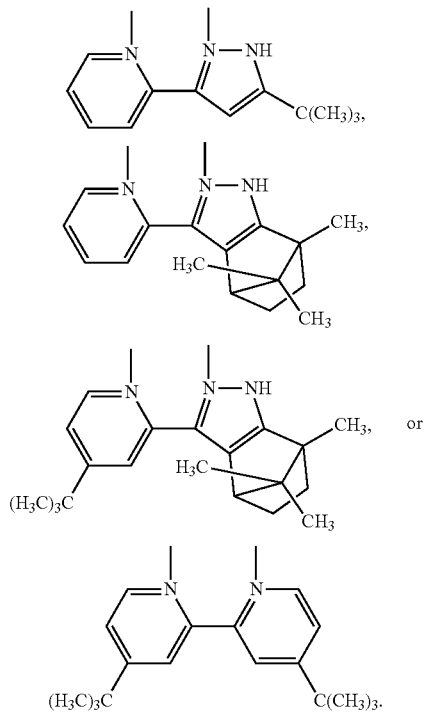

* * * * *